US010244987B2

(12) United States Patent
Chong et al.

(10) Patent No.: US 10,244,987 B2
(45) Date of Patent: Apr. 2, 2019

(54) PHYSIOLOGICAL DETECTION SYSTEM WITH ADJUSTABLE SIGNAL SOURCE AND OPERATING METHOD THEREOF

(71) Applicant: PIXART IMAGING INC., Hsin-Chu County (TW)

(72) Inventors: Sheau-Foong Chong, Santa Clara, CA (US); Chun-Wei Chen, Santa Clara, CA (US)

(73) Assignee: PIXART IMAGING INC., Hsin-Chu County (TW)

( * ) Notice: Subject to any disclaimer, the term of this patent is extended or adjusted under 35 U.S.C. 154(b) by 504 days.

(21) Appl. No.: 14/825,272

(22) Filed: Aug. 13, 2015

(65) Prior Publication Data
US 2017/0042484 A1 Feb. 16, 2017

(51) Int. Cl.
*A61B 5/00* (2006.01)
*A61B 5/1455* (2006.01)
*A61B 5/024* (2006.01)

(52) U.S. Cl.
CPC ........ *A61B 5/7221* (2013.01); *A61B 5/02416* (2013.01); *A61B 5/1455* (2013.01); *A61B 5/14551* (2013.01)

(58) Field of Classification Search
None
See application file for complete search history.

(56) References Cited

U.S. PATENT DOCUMENTS

| 4,458,518 A | * | 7/1984 | Ingle | G01D 18/00 600/501 |
| 4,859,057 A | * | 8/1989 | Taylor | A61B 5/14551 600/323 |
| 4,914,512 A | * | 4/1990 | Sekiguchi | A61B 1/042 348/453 |
| 5,717,605 A | * | 2/1998 | Komiya | G01J 3/02 250/578.1 |
| 8,374,682 B2 | * | 2/2013 | Freeman | A61B 5/0059 600/473 |
| 2002/0020818 A1 | * | 2/2002 | Mitchell | G01N 21/6408 250/459.1 |
| 2002/0035330 A1 | * | 3/2002 | Cline | A61B 1/00009 600/476 |
| 2002/0161282 A1 | * | 10/2002 | Fulghum | A61B 1/00009 600/160 |
| 2007/0024946 A1 | * | 2/2007 | Panasyuk | A61B 5/0059 359/253 |
| 2011/0077486 A1 | * | 3/2011 | Watson | A61B 5/021 600/324 |
| 2012/0197137 A1 | * | 8/2012 | Jeanne | A61B 5/02028 600/479 |
| 2013/0102907 A1 | * | 4/2013 | Funane | A61B 5/0075 600/476 |

(Continued)

Primary Examiner — Tse Chen
Assistant Examiner — Joanne Hoffman
(74) Attorney, Agent, or Firm — Hauptman Ham, LLP

(57) ABSTRACT

A physiological detection system including a light source module, a photo sensor and a processor is provided. The light source module is configured to provide light to illuminate a skin region. The photo sensor is configured to detect emergent light passing the skin region with at least one signal source parameter and output an image signal. The processor is configured to calculate a confident level according to the image signal to accordingly adjust the at least one signal source parameter.

20 Claims, 6 Drawing Sheets

(56) References Cited

U.S. PATENT DOCUMENTS

| | | | | |
|---|---|---|---|---|
| 2013/0324855 | A1* | 12/2013 | Lisogurski | A61B 5/0205 600/476 |
| 2014/0039309 | A1* | 2/2014 | Harris | A61B 5/7282 600/431 |
| 2015/0018649 | A1* | 1/2015 | Lisogurski | H05B 33/0842 600/323 |
| 2015/0031971 | A1* | 1/2015 | Lisogurski | A61B 5/14552 600/324 |
| 2015/0157220 | A1* | 6/2015 | Fish | A61B 5/02055 600/301 |
| 2015/0193669 | A1* | 7/2015 | Gu | G06K 9/46 348/77 |
| 2015/0208962 | A1* | 7/2015 | Baker, Jr. | A61B 5/1495 600/331 |
| 2016/0029964 | A1* | 2/2016 | LeBoeuf | A61B 5/0205 600/476 |
| 2016/0198961 | A1* | 7/2016 | Homyk | A61B 5/0082 600/476 |

\* cited by examiner

PHYSIOLOGICAL DETECTION SYSTEM WITH ADJUSTABLE SIGNAL SOURCE AND OPERATING METHOD THEREOF

BACKGROUND

1. Field of the Disclosure

This disclosure generally relates to an optical physiological detection system and, more particularly, to a physiological detection system with adjustable signal source and an operating method thereof.

2. Description of the Related Art

Conventional pulse oximeters utilize a noninvasive method to monitor the blood oxygenation and the heart rate of a user. The conventional pulse oximeters generally emit a red light beam (wavelength of about 660 nm) and an infrared light beam (wavelength of about 910 nm) to penetrate a part of the human body and detect an intensity variation of penetrating light based on that the oxyhemoglobin and the deoxyhemoglobin have different absorptivities in particular spectrum. After the intensity variation of the penetrating light, e.g. photoplethysmography signal or so called PPG signal, of the two wavelengths is detected, the blood oxygenation can then be calculated according to the following equation:

Oxygen saturation=100%×[HbO2]/([HbO2]+[Hb])

wherein [HbO2] is oxyhemoglobin concentration; and [Hb] is deoxyhemoglobin concentration.

Generally, the intensity variation of the penetrating light of the two wavelengths detected by a pulse oximeter becomes strong and weak with the heartbeat. This is because blood vessels will expand and contract with the heartbeat such that the blood volume that the light beams pass through will change to accordingly change the ratio of light energy being absorbed. Accordingly, it is able to calculate a physiological characteristic of the user according to the detected PPG signal(s).

However, when an optical physiological detection device is applied to a portable device or a wearable device, a detection surface thereof can have a relative movement with respect to a skin surface or the detection surface is not tightly attached to the skin surface such that the signal quality of detected signals is reduced to degrade the detection accuracy.

SUMMARY

Accordingly, the present disclosure provides a physiological detection system with high accuracy and an operating method thereof so as to increase the applicable range thereof.

The present disclosure provides a physiological detection system with adjustable signal source and an operating method thereof that improve the signal quality and detection accuracy by adjusting at least one signal source parameter.

The present disclosure provides a physiological detection system including a physiological detection module. The physiological detection module includes a light source module, a photo sensor and a first processor. The light source module is configured to provide light to illuminate a skin region. The photo sensor is configured to detect emergent light passing the skin region with at least one signal source parameter and output an image signal. The first processor is configured to calculate a first confident level according to the image signal and update the at least one signal source parameter according to the first confident level.

The present disclosure further provides an operating method of a physiological detection system. The physiological detection system includes a physiological detection module. The operating method includes the steps of: detecting, by the physiological detection module, emergent light from a skin region with at least one signal source parameter to generate an image signal; calculating, by the physiological detection module, a confident level according to the image signal; comparing, by the physiological detection module, the confident level with at least one threshold; and updating, by the physiological detection module, the at least one signal source parameter according to a comparison result of comparing the confident level and the at least one threshold.

The present disclosure further provides an operating method of a physiological detection system. The physiological detection system includes a physiological detection module and an application module coupled to each other. The operating method includes the steps of: detecting, by the physiological detection module, emergent light from a skin region with at least one signal source parameter to generate an image signal; calculating, by the physiological detection module, a first confident level according to the image signal; outputting, by the physiological detection module, an intensity variation signal according to a plurality of image signals; calculating, by the application module, a second confident level according to the intensity variation signal; and updating the at least one signal source parameter according to the first confident level and the second confident level.

In the physiological detection system and operating method according to the present disclosure, the confident level includes, for example, at least one of an average brightness value, uniformity, a photoplethysmography (PPG) signal amplitude, a signal to noise ratio (SNR) and other image quality parameters. The signal source parameter includes, for example, at least one of an exposure time, a gain value, a window of interest (WOI), a light emitting intensity, a focus length and a light receiving phase.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
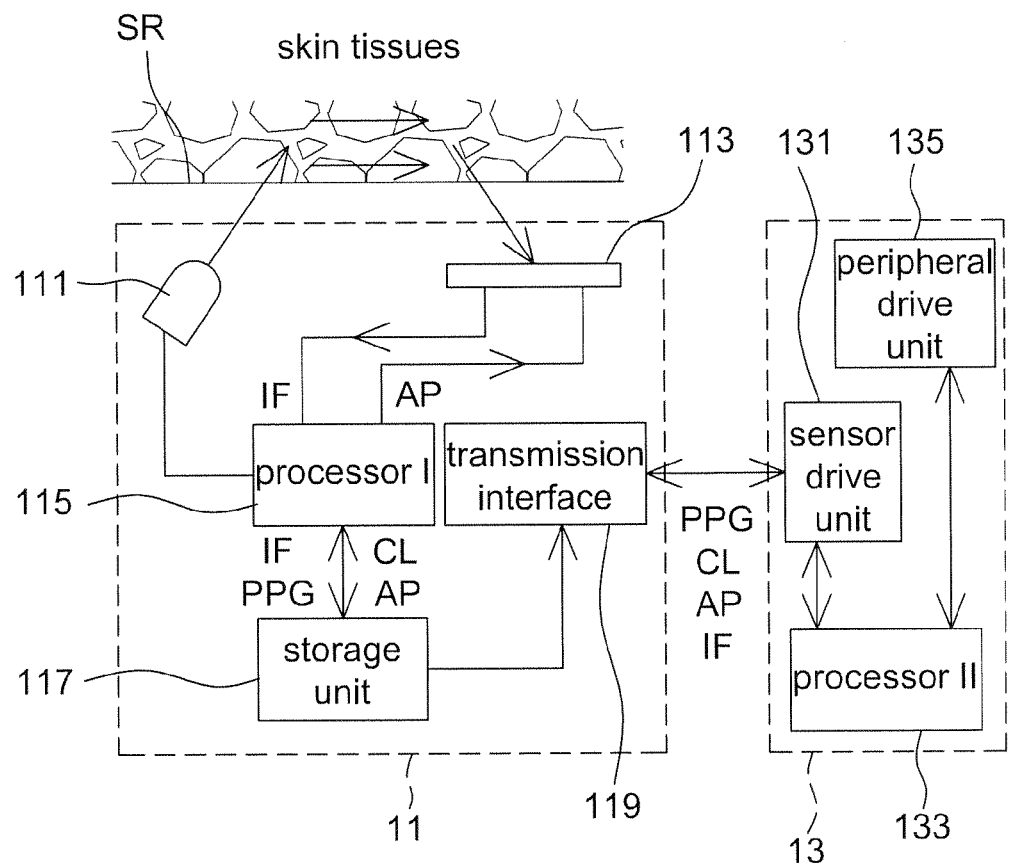
FIG. 1 is a schematic block diagram of a physiological detection system according to one embodiment of the present disclosure.

Referring to FIG. 1, it is a schematic block diagram of a physiological detection system 100 according to one embodiment of the present disclosure. The physiological detection system 100 includes a physiological detection module 11 and an application module 13 coupled to each other. The physiological detection module 11 is configured to emit light toward a skin region SR to penetrate a part of body tissues and detect emergent light passing the skin region SR to generate an image signal IF, wherein the skin region SR is at different parts of the human body according to different applications, e.g. the finger, ankle, wrist, ear or forehead, without particular limitations. The application module 13 is one of a portable electronic device, a wearable electronic device, a home appliance, a vehicle device and a medical device. The application module 13 communicates with the physiological detection module 11, e.g. sending data, in a wired or wireless manner, and presents the detected physiological characteristics.

It should be mentioned that although FIG. 1 shows that the physiological detection module 11 and the application module 13 are separated, the present disclosure is not limited thereto. In other embodiments, the physiological detection module 11 is integrated in the application module 13.

The physiological detection module 11 includes a light source module 111, a photo sensor 113, a first processor 115, a storage unit 117 and a transmission interface 119.

The light source module 111 includes, for example, a coherent light source, a partially coherent light source or a non-coherent light source without particular limitations, e.g. including a light emitting diode or a laser diode. The light source module 111 is configured to provide light to illuminate a skin region SR, and after entering skin tissues of the skin region SR, the light propagates a distance and then ejects from the skin region SR, wherein the light intensity of emergent light fluctuates with time due to a part of light energy being absorbed by blood. In some embodiments, an emission wavelength of the light source module 111 is that used in conventional pulse oximeters. In other embodiments, an emission wavelength of the light source module 111 is between 300 nm and 940 nm. It should be mentioned that although FIG. 1 shows a single light source, it is only intended to illustrate but not to limit the present disclosure. In some embodiments, when the physiological detection system 100 is used to detect the blood oxygenation, the light source module 111 includes two light sources respectively configured to emit red light and infrared light. In other embodiments, when the physiological detection system 100 has the correction function, the light source module 111 includes three light sources respectively configured to emit green light, red light and infrared light, wherein a PPG signal associated with the green light is configured to determine a filter parameter which is used to filter PPG signals associated with the red light and the infrared light. In other embodiments, in order to change the light emitting intensity of the light source module 111, the light source module 111 includes a plurality of light sources emitting light of a same wavelength or includes a light source with adjustable drive current.

Figure 2:
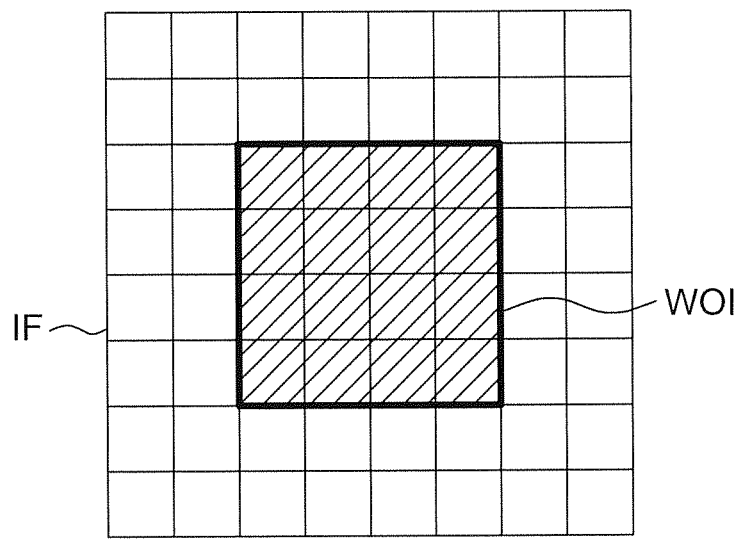
FIG. 2 is a schematic diagram of a window of interest of a pixel array according to one embodiment of the present disclosure.

The photo sensor 113 is configured to detect emergent light passing the skin region SR with at least one signal source parameter, and output an image signal IF at every sample period. Accordingly, image signals IF corresponding to a plurality of sample periods form an intensity variation signal. In some embodiments, the photo sensor 113 is a photo diode, and the intensity variation signal outputted therefrom is configured as the PPG signal. In some embodiments, the photo sensor 113 is an image sensor which includes a pixel array having a plurality of pixels. Every pixel of the pixel array outputs an image signal IF in an image frame and the first processor 115 is configured to calculate a sum of image signals of a plurality of pixels of the image frame, wherein the variation of the sum of image signals with time is configured as a PPG signal. In some embodiments, the variation of image signals IF with time outputted by each of the pixels of the pixel array is configured as a PPG signal, i.e. the photo sensor 113 outputting a plurality of intensity variation signals. In addition, in some embodiments, when the photo sensor 113 is an image sensor, it is preferably an active image sensor, e.g. a CMOS image sensor, such that a window of interest (WOI) as shown in FIG. 2 is selectable according to the signal distribution actually detected by the pixel array. It is appreciated that a position of the window of interest (WOI) is not limited to that shown in FIG. 2.

Figure 3:
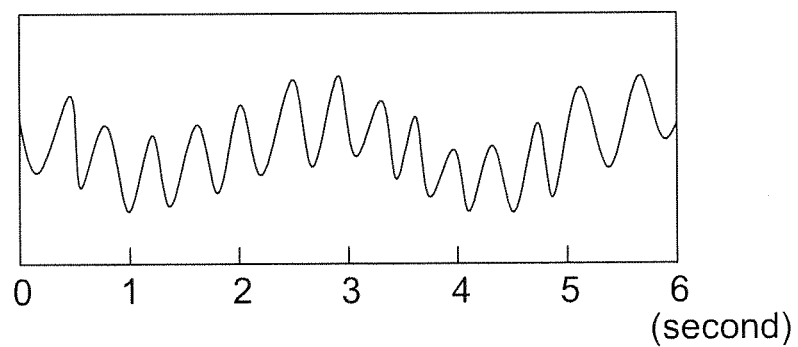
FIG. 3 is a schematic diagram of an intensity variation signal generated by a physiological detection system according to one embodiment of the present disclosure.

The first processor 115 is, for example, a digital signal processor (DSP) and is configured to receive image signals IF outputted from the photo sensor 113 for post-processing, e.g. generating an intensity variation signal according to a plurality of image signals IF to be configured as the PPG signal. For example, the first processor 115 receives the image signal IF from the photo sensor 113 and successively retrieves a plurality of image signals IF within a time interval, e.g. 5-10 seconds, to be configured as the PPG signal. For example, FIG. 3 shows the intensity variation signal within a time interval of 6 seconds configured as the PPG signal, but the present disclosure is not limited thereto. FIG. 3 is a schematic diagram of an intensity variation signal (or PPG signal) generated by the physiological detection system according to one embodiment of the present disclosure. As the photo sensor 113 sequentially outputs image signals IF at a sample frequency (or frame rate), the time intervals are partially overlapped or not overlapped with each other in time. For example, the first processor 115 takes the intensity variation signal within 0-6 seconds as a PPG signal, and then takes the intensity variation signal within 1-7 seconds as a next PPG signal or takes the intensity variation signal within 7-13 seconds as a next PPG signal and so forth.

When the photo sensor 113 is a photodiode, the first processor 115 directly retrieves the intensity variation signal outputted by the photo sensor 113 as the PPG signal, wherein the first processor 115 does not process the intensity variation signal. In some embodiments, the first processor 115 performs only the pre-processing, such as the filtering or amplifying, on the intensity variation signal to generate the PPG signal.

When the photo sensor 113 is an image sensor, the first processor 115 calculates a sum of image signals (e.g. implemented by software) of at least a part of pixels (e.g. within the WOI) of every image frame outputted by the pixel array, and successively calculates the sum of image signals for a time interval. e.g. 5-10 seconds, to be configured as the PPG signal, as shown in FIG. 3. In other embodiments, when the photo sensor 113 is an image sensor and the image sensor itself has the function of calculating the sum of image signals (e.g. implemented by hardware), the first processor 115 retrieves the sum of image signals for a time interval, e.g. 5-10 seconds, to be configured as the PPG signal; and in this embodiment, the first processor 115 does not process the sum of image signals or performs only the pre-processing on the sum of image signals such as the filtering or amplifying. In other words, the PPG signal herein is the time variation of image signals outputted by a photodiode, or the time variation of image signals of a single pixel or the sum of image signals of a plurality of pixels.

In this embodiment, the first processor 115 is configured to calculate a first confident level according to the image signal IF and update at least one signal source parameter AP according to the first confident level.

In one embodiment, the first confident level includes at least one of an average brightness value and uniformity. During operation, a detection surface of the physiological detection module 11 is preferably tightly attached to the skin region SR to prevent ambient light from being received by the photo sensor 113. Accordingly, an average brightness value of the image signal IF outputted by the photo sensor 113 is preferably lower than a first brightness threshold to make sure that the photo sensor 113 does not receive the ambient light. In addition, in order to be able to use the image signal IF outputted by the photo sensor 113 to calculate physiological characteristics, an average brightness value of the image signal IF outputted by the photo sensor 113 is preferably higher than a second brightness threshold to make sure that the photo sensor 113 receives enough emergent light. In another embodiment, when the photo sensor 113 includes a pixel array, uniformity of the image frame (i.e. the image signal IF) outputted by the photo sensor 113 is preferably higher than a predetermined threshold to make sure that the image quality of the image frame is good enough for calculating physiological characteristics. When the first confident level does not satisfy a predetermined condition (e.g. the above thresholds), the first processor 115 updates the at least one signal source parameter AP, wherein the predetermined condition is satisfied when, for example, the first confident level is within a threshold range, larger than a threshold or smaller than a threshold depending on the first confident level being used.

Figure 4:
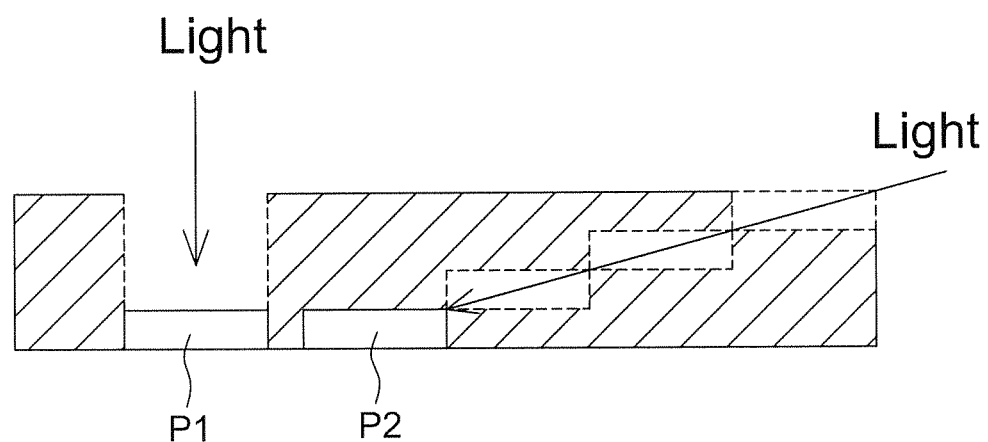
FIG. 4 is a schematic diagram of different light receiving phases according to one embodiment of the present disclosure.

In one embodiment, the at least one signal source parameter AP is selected from a group consisting of an exposure time, a gain value, a window of interest (WOI), a focus length and a light receiving phase. The exposure time is referred to an exposure time of each sample period of the photo sensor 113. The gain value is referred to a gain (e.g. analog or digital gain) for amplifying detected signals of the photo sensor 113. The window of interest is used to select a pixel area, e.g. shown in FIG. 2, having a higher confident level or having brightness within a predetermined range. The focus length is adjusted, for example, by a motor (e.g. a voice coil motor). The receiving phase is used to change a phase of emergent light received from the skin region SR. For example, referring to FIG. 4, it shows that two pixels P1 and P2 respectively receive emergent light at different angles (or phases), and the region filled with oblique lines is referred to the opaque metal layer, e.g. forming different light tunnels by a plurality of metal layers (e.g. M1-M10) in the CMOS process such that different pixels receive emergent light at different angles (or phases). It should be mentioned that although FIG. 4 shows only two pixels, it is only intended to illustrate but not to limit the present disclosure. The number of pixels receiving emergent light at a same phase is determined according to different applications without particular limitations. It is appreciated that when the photo sensor 113 includes a single photodiode, the at least one signal source parameter AP does not include the window of interest (WOI) and the light receiving phase.

In other embodiments, the at least one signal source parameter AP is further configured to control a light emitting intensity of the light source module 111, e.g. adjusting the light emitting intensity by changing the drive current, the number of light sources being activated or a light source distance.

The storage unit 117 is, for example, a register or a memory, e.g. RAM. The storage unit 117 is coupled to the first processor 115 and configured to temporarily store the image signal IF, the intensity variation signal (or PPG signal), the first confident level CL, the at least one signal source parameter AP and algorithms.

The transmission interface 119 is configured to communicate with an external device, e.g. sending the image signal IF, the intensity variation signal (or PPG signal), the first confident level CL and/or the signal source parameter AP to the external device. The transmission interface 119 is, for example, a wired transmission interface (e.g. I2C, SPI, USB or the like) or a wireless transmission interface (e.g. Bluetooth interface).

The application module 13 is coupled to the physiological detection module 11 to be configured as the external device of the physiological detection module 11. The application module 13 is configured to receive the image signal IF, the intensity variation signal (or PPG signal), the first confident level CL and/or the signal source parameter AP to perform corresponding processes and controls, wherein the first confident level CL is served as a reference for further adjusting the signal source parameter AP. The application module 13 informs the physiological detection module 11 to output data and sends the updated signal source parameter AP back to the physiological detection module 11. The application module 13 includes a sensor drive unit 131, a second processor 133 and a peripheral drive unit 135.

The sensor drive unit 131 is configured to drive the physiological detection module 11 and setup the wired or wireless communication to the transmission interface 119 so as to receive the image signal IF, the intensity variation signal (or PPG signal), the first confident level CL and/or the signal source parameter AP from the transmission interface 119 and send the updated signal source parameter AP back to the transmission interface 119. In other words, the sensor drive unit 131 also includes a transmission interface. In the present disclosure, the at least one signal source parameter AP is updated according to the first confident level and/or a second confident level (calculated by the application module 13). The method of transmitting data between two devices in a wired or wireless manner is known to the art and thus details thereof are not described herein.

The second processor 133 is, for example, a microcontroller (MCU) or a central processing unit (CPU) and is configured to calculate a second confident level according to the intensity variation signal (or PPG signal). The second processor 133 is further configured to update the at least one signal source parameter AP when necessary. In one embodiment, the second confident level includes, for example, at least one of a PPG signal amplitude and a signal to noise ratio.

For example, after receiving the PPG signal (e.g. shown in FIG. 3), the second processor 133 compares the amplitude of the PPG signal with at least one threshold. When the PPG signal amplitude is within a predetermined threshold range, it means that the emergent light detected by the photo sensor 113 is suitable to calculate physiological characteristics such that the at least one signal source parameter AP is not adjusted. When the PPG signal amplitude is not within the predetermined threshold range, the at least one signal source parameter AP is adjusted.

Figure 5:
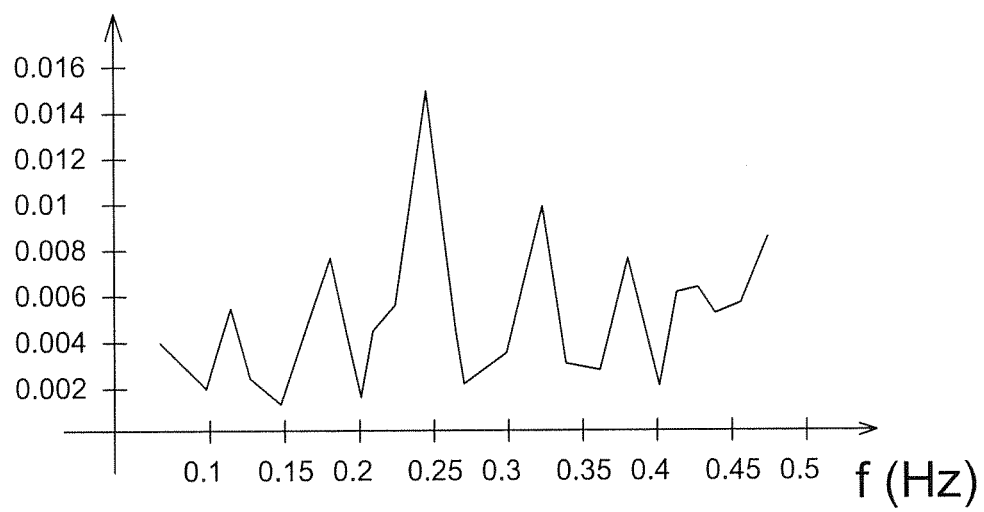
FIG. 5 is a schematic diagram of frequency domain data generated by a physiological detection system according to one embodiment of the present disclosure.

For example, the second processor 133 converts the intensity variation signal to the frequency domain at first as shown in FIG. 5. FIG. 5 is a schematic diagram of frequency domain data generated by the physiological detection system according to one embodiment of the present disclosure. The second processor 133 calculates a ratio between a target spectrum (e.g. with maximum spectrum energy or a predetermined spectrum) and a sum of other spectrum energy to be configured as a signal to noise ratio (SNR). Then, the second processor 133 compares the SNR with at least one threshold. For example, when the SNR is larger than a predetermined threshold, the at least one signal source parameter AP is not adjusted; whereas when the SNR is smaller than the predetermined threshold, the at least one signal source parameter AP is adjusted.

The second processor 133 is further configured to calculate physiological characteristics according to the intensity variation signal (or PPG signal), wherein the physiological characteristics include, for example, a blood oxygenation, a heart rate, a respiration rate, a second derivative of photoplethysmogram (SDPPG) or the like. The method of calculating the physiological characteristics according to the PPG signal is known to the art and thus details thereof are not described herein.

The peripheral drive unit 135 is configured to drive a peripheral device to present the physiological characteristics, e.g. driving a display to show the physiological characteristics or give a warning, or driving a speaker to play the physiological characteristics or give a warning, wherein the method of driving a peripheral device is known to the art and thus details thereof are not described herein.

Figure 6:
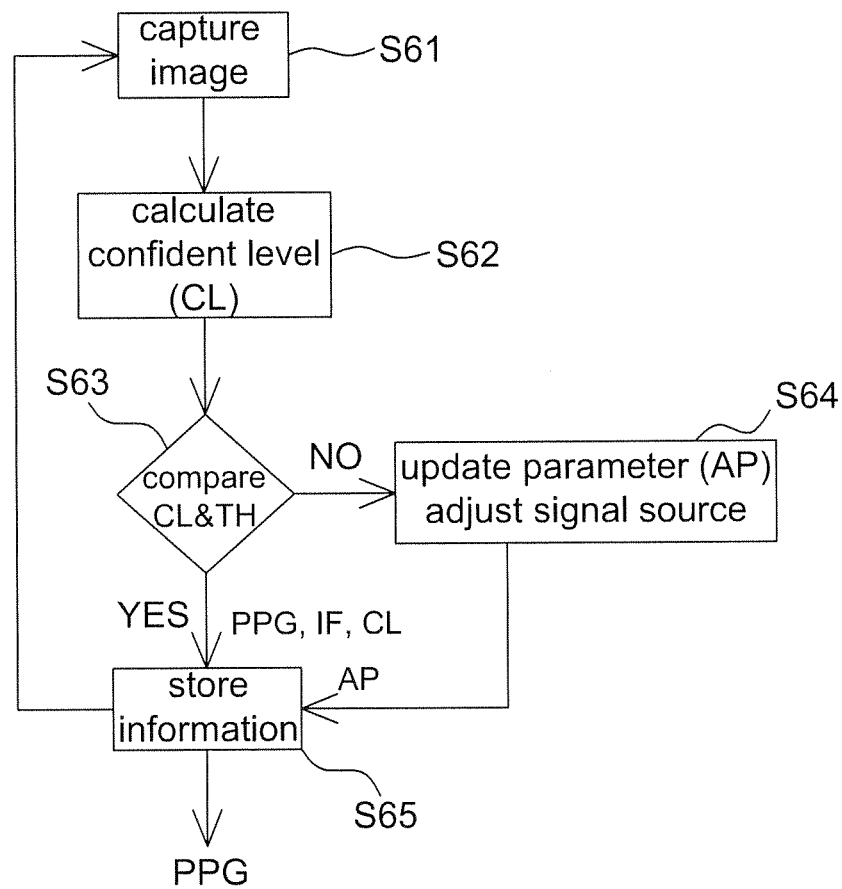
FIG. 6 is a flow chart of an operating method of a physiological detection system according to a first embodiment of the present disclosure.

Referring to FIG. 6, it is a flow chart of an operating method of a physiological detection system according to a first embodiment of the present disclosure, which includes the steps of: capturing an image (Step S61); calculating a confident level (Step S62); comparing the confident level with at least one threshold (Step S63); updating at least one signal source parameter and adjusting signal source (Step S64); and storing information (Step S65). The operating method of this embodiment is applicable to the physiological detection system 100 of FIG. 1.

Referring to FIGS. 1-4 and 6 together, details of the first embodiment is illustrated hereinafter.

Step S61: The physiological detection module 11 detects emergent light from a skin region SR with at least one signal source parameter AP to generate an image signal IF. For example, the light source module 111 of the physiological detection module 11 illuminates at the skin region SR and the photo sensor 113 of the physiological detection module 11 detects the emergent light from the skin region SR to generate an image signal IF in every sample period.

Step S62: The physiological detection module 11 calculates a confident level CL according to the image signal IF. For example, the first processor 115 of the physiological detection module 11 calculates at least one of an average brightness value and uniformity to be configured as the confident level CL. When the photo sensor 113 includes a pixel array, the first processor 115 calculates an average brightness value or uniformity of the whole image frame outputted by the pixel array, or calculates an average brightness value or uniformity of a part of (e.g. the window of interest in FIG. 2) image frame outputted by the pixel array.

Step S63: The first processor 115 of the physiological detection module 11 compares the confident level CL with at least one threshold, wherein the at least one threshold is previously stored in the storage unit 117 of the physiological detection module 11. A number of the at least one threshold is determined according to different applications. For example, the first processor 115 compares the confident level CL with a plurality of thresholds to confirm whether the confident level CL is within a predetermined threshold range, wherein the predetermined threshold range indicates that the image signal IF is a valid image signal and suitable to perform the following calculation. For example, the first processor 115 compares the confident level CL with a single threshold to confirm whether the confident level CL is larger than (or equal to) or smaller than (or equal to) the single threshold.

Step S64: When the confident level CL is not within the predetermined threshold range, the at least one signal source parameter AP is updated according to a comparison result of comparing the confident level CL and the at least one threshold, and the signal source is adjusted. For example, when the at least one signal source parameter AP includes an exposure time, the first processor 115 adjusts the exposure time of the photo sensor 113. For example, when the at least one signal source parameter AP includes a gain value, the first processor 115 adjusts the gain of the photo sensor 113. For example, when the at least one signal source parameter AP includes a window of interest (as shown in FIG. 2), the first processor 115 adjusts the size and position of the window of interest. For example, when the at least one signal source parameter AP includes a focus length, the first processor 115 controls a motor to adjust the setting of focus length of the photo sensor 113. For example, when the at least one signal source parameter AP includes a light receiving phase, the first processor 115 changes the pixel of the photo sensor 113 that outputs the image signal IF, e.g. deactivating the pixel P1 and activating the pixel P2 shown in FIG. 4, or vice versa. In this embodiment, when a plurality of signal source parameters AP are included, the first processor 115 adjusts a part of the signal source parameters AP each time or adjusts all of the signal source parameters AP at the same time. For example, the storage unit 117 previously stores a lookup table, and the first processor 115 compares the confident level CL with the lookup table to update the at least one signal source parameter AP. After the at least one signal source parameter AP is updated, the first processor 115 adjusts the signal source according to the updated signal source parameter AP.

Step S65: The first processor 115 generates an intensity variation signal (or PPG signal), as shown in FIG. 3, according to a plurality of image signals IF to be stored in the storage unit 117, and the intensity variation signal (or PPG signal) is outputted through the transmission interface 119 thereof. In addition, other related information, such as the image signal IF, the confident level CL and the signal source parameter AP, is also stored in the storage unit 117 to be used later.

Next, the physiological detection module 11 generates a next image signal according to the updated signal source parameter AP.

Figure 7:
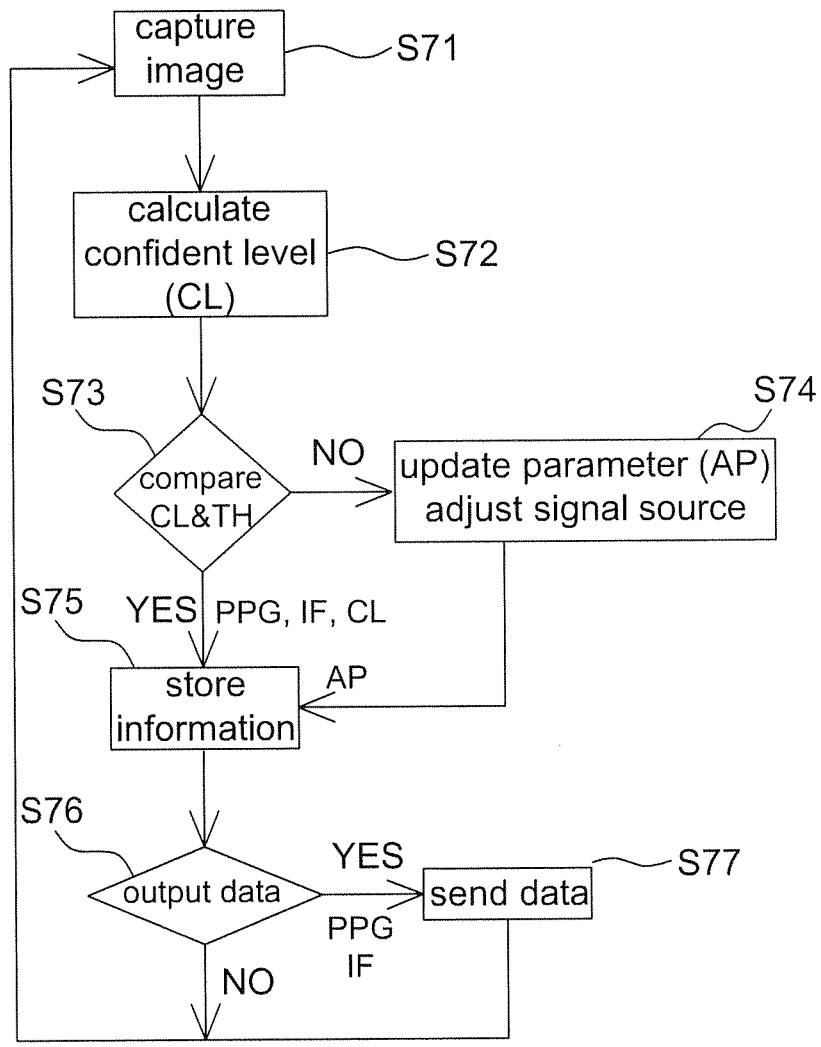
FIG. 7 is a flow chart of an operating method of a physiological detection system according to a second embodiment of the present disclosure.

Referring to FIG. 7, it is a flow chart of an operating method of a physiological detection system according to a second embodiment of the present disclosure, which includes the steps of: capturing an image (Step S71); calculating a confident level (Step S72); comparing the confident level with at least one threshold (Step S73); updating at least one signal source parameter and adjusting signal source (Step S74); storing information (Step S75); identifying whether to output the stored data (Step S76); and sending data (Step S77). The operating method of this embodiment is applicable to the physiological detection system 100 of FIG. 1.

The Steps S71-S75 of the second embodiment are similar to the Steps S61-S65 of the first embodiment and thus details thereof are not repeated herein. In the second embodiment, after the information is stored in Step S75, in Step S76 the transmission interface 119 of the physiological detection module 11 confirms whether a data sending signal, e.g. a polling signal or an interruption signal, is received from the application module 13. If the receiving of the data sending signal is confirmed, the transmission interface 119 sends the image signal IF, PPG signal, confident level CL (obtained in Step S72) and signal source parameter AP (stored in the storage unit 117) to the application module 13 (Step S77). If the data sending signal is not received, the data is not sent by the transmission interface 119. Finally, the physiological detection module 11 generates a next image signal with the updated signal source parameter AP (updated in Step S74).

In the second embodiment, after receiving the intensity variation signal (or PPG signal), the application module 13 calculates physiological characteristics according to the intensity variation signal and performs corresponding controls.

Figure 8:
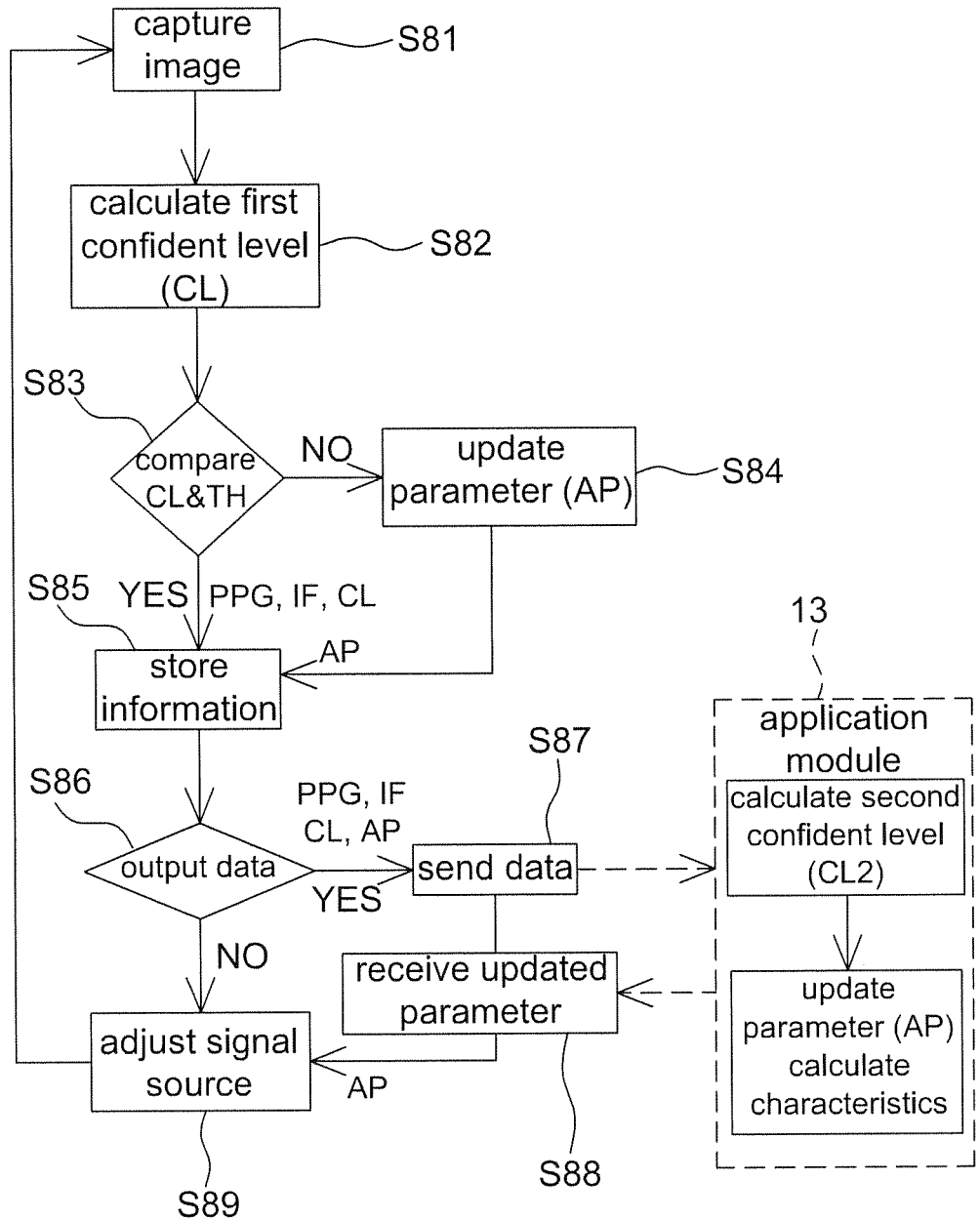
FIG. 8 is a flow chart of an operating method of a physiological detection system according to a third embodiment of the present disclosure.

Referring to FIG. 8, it is a flow chart of an operating method of a physiological detection system according to a third embodiment of the present disclosure, which includes the steps of: capturing an image (Step S81); calculating a first confident level (Step S82); comparing the first confident level with at least one threshold (Step S83); updating at least one signal source parameter (Step S84); storing information (Step S85); identifying whether to output the stored data (Step S86); sending data (Step S87); receiving updated signal source parameter (Step S88); and adjusting signal source (Step S89). The operating method of this embodiment is applicable to the physiological detection system 100 of FIG. 1. In this embodiment, the Steps S81-S83 and Step 85 are similar to the Steps S61-S63 and Step 65 of the above first embodiment, and thus details thereof are not repeated herein.

The difference between the third embodiment and the second embodiment is that, in the third embodiment, the application module 13 further calculates a second confident level CL2 according to the received intensity variation signal (or PPG signal) so as to further update the signal source parameter AP if necessary. Accordingly, in Step S84 of the third embodiment, the physiological detection module 11 only updates the at least one signal source parameter AP according to a comparison result of comparing a first confident level CL and at least one threshold, but the signal source is not yet adjusted. In this embodiment, the first confident level CL includes, for example, at least one of an average brightness value and uniformity.

Steps S86-S87: When the physiological detection module 11 confirms that a data sending signal (e.g. a polling signal or interruption signal) is received from the application module 13, the physiological detection module 11 outputs an intensity variation signal (or PPG signal), which is generated according to a plurality of image signals IF, to the application module 13. If the data sending signal is not received, Step S89 is directly entered such that the physiological detection module 11 adjusts the corresponded sampling setting according to the current signal source parameter AP (e.g. updated in Step S84), e.g. adjusting at least one of the exposure time, gain value, window of interest, focus length and light receiving phase.

After receiving the intensity variation signal (or PPG signal), the application module 13 calculates a second confident level CL2 according to the intensity variation signal (or PPG signal), wherein the second confident level CL2 includes, for example, at least one of a PPG signal amplitude and a signal to noise ratio, which are described above and thus details thereof are not repeated herein. The application module 13 further updates the at least one signal source parameter AP according to the second confident level CL2 when necessary, e.g. when the PPG signal amplitude is not within a predetermined range or the SNR does not exceed a predetermined threshold, and sends back the updated signal source parameter AR In addition, the application module 13 further calculates physiological characteristics according to the intensity variation signal (or PPG signal) and presents the physiological characteristics, e.g. a blood oxygenation, heart rate, respiration rate, SDPPG or the like.

Step S88-S89: After receiving the updated signal source parameter AP from the application module 13, the physiological detection module 11 adjusts the corresponded sampling setting according to the updated signal source parameter AP.

Next, the physiological detection module 11 generates a next image signal according to the updated signal source parameter AP. In some embodiments, the signal source parameter AP is further configured to adjust a light emitting intensity of the light source module 111 of the physiological detection module 11.

It should be mentioned that although FIG. 1 shows that the light source module 111 and the photo sensor 113 are disposed at the same side of the skin region SR to form the reflective detection device, the present disclosure is not limited thereto. In other embodiments, the light source module 111 and the photo sensor 113 are disposed at opposite sides of a skin region to form a transmissive detection device.

It is appreciated that in the above embodiments when the first confident level and/or the second confident level satisfy the predetermined requirement, it means that the image signal IF captured by the photo sensor 113 is suitable to calculate physiological characteristics and thus the at least one signal source parameter AP is not adjusted.

As mentioned above, when the optical physiological detection system is applied to portable devices or wearable devices, the detection accuracy is decreased due to the uncertainty of the usage conditions. Therefore, the present disclosure further provides a physiological detection system (FIG. 1) and an operating method thereof (FIGS. 6-8) that adjust at least one signal source parameter according to the confident level of image signals so as to improve the detection accuracy.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A physiological detection system, comprising:
   a physiological detection module comprising:
   a light source configured to provide light to illuminate a skin region;
   a photo sensor comprising a first pixel and a second pixel, and configured to detect emergent light passing the skin region with at least one signal source parameter and output an image signal, wherein the photo sensor further comprises opaque metal layers around the first pixel and the second pixel to respectively form an overhead first light tunnel toward the first pixel and a stepped second light tunnel toward the second pixel to cause the first pixel and the second pixel to receive the emergent light from the skin region at different first and second light receiving angles respectively, and the different first and second light receiving angles define the at least one signal source parameter, and a first processor configured to calculate a first confident level according to the image signal and update the at least one signal source parameter according to the first confident level.

2. The physiological detection system as claimed in claim 1, wherein the first confident level comprises at least one of an average brightness value and uniformity.

3. The physiological detection system as claimed in claim 1, wherein
the at least one signal source parameter further comprises at least one of an exposure time, a gain value, a window of interest, and a focus length, and
the window of interest is a pixel area of the photo sensor having a higher confident level than other pixels or having brightness within a predetermined range.

4. The physiological detection system as claimed in claim 1, wherein an emission wavelength of the light source is between 300 nm and 940 nm.

5. The physiological detection system as claimed in claim 1, wherein the at least one signal source parameter is further configured to control a light emitting intensity of the light source.

6. The physiological detection system as claimed in claim 1, wherein the physiological detection module further comprises a transmission interface coupled to the first processor,
the first processor is further configured to generate an intensity variation signal according to a plurality of image signals, and
the transmission interface is configured to output the intensity variation signal.

7. The physiological detection system as claimed in claim 6, wherein the physiological detection system further comprises an application module coupled to the physiological detection module, and the application module comprises a second processor configured to calculate physiological characteristics according to the intensity variation signal.

8. The physiological detection system as claimed in claim 6, wherein the physiological detection system further comprises an application module coupled to the physiological detection module, and the application module comprises a second processor configured to calculate a second confident level according to the intensity variation signal and update the at least one signal source parameter according to the second confident level.

9. The physiological detection system as claimed in claim 8, wherein the second confident level comprises at least one of a PPG signal amplitude and a signal to noise ratio.

10. The physiological detection system as claimed in claim 7, wherein the application module is selected from a group consisting of a portable electronic device, a wearable electronic device, a home appliance, a vehicle device and a medical device.

11. An operating method of a physiological detection system, the physiological detection system comprising a physiological detection module which comprises a photo sensor having a first pixel and a second pixel, the operating method comprising:
detecting, by the physiological detection module, emergent light from a skin region with at least one signal source parameter to generate an image signal, wherein the photo sensor further comprises opaque metal layers around the first pixel and the second pixel to respectively form an overhead first light tunnel toward the first pixel and a stepped second light tunnel toward the second pixel to cause the first pixel and the second pixel to receive the emergent light from the skin region at different first and second light receiving angles respectively, and the different first and second light receiving angles define the at least one signal source parameter;
calculating, by the physiological detection module, a confident level according to the image signal;
comparing, by the physiological detection module, the confident level with at least one threshold; and
updating, by the physiological detection module, the at least one signal source parameter according to a comparison result of comparing the confident level and the at least one threshold.

12. The operating method as claimed in claim 11, wherein the confident level comprises at least one of an average brightness value and uniformity.

13. The operating method as claimed in claim 11, wherein
the at least one signal source parameter further comprises at least one of an exposure time, a gain value, a window of interest, and a focus length, and
the window of interest is a pixel area of the physiological detection module having a higher confident level than other pixels or having brightness within a predetermined range.

14. The operating method as claimed in claim 11, further comprising:
generating, by the physiological detection module, an intensity variation signal according to a plurality of image signals; and
outputting, by the physiological detection module, the intensity variation signal.

15. The operating method as claimed in claim 14, wherein the physiological detection system further comprises an application module coupled to the physiological detection module, and the operating method further comprises:
receiving the intensity variation signal with the application module; and
calculating, by the application module, physiological characteristics according to the intensity variation signal.

16. An operating method of a physiological detection system, the physiological detection system comprising a physiological detection module, which comprises a photo sensor having a first pixel and a second pixel, and an application module coupled to each other, the operating method comprising:
detecting, by the physiological detection module, emergent light from a skin region with at least one signal source parameter to generate an image signal, wherein the photo sensor further comprises opaque metal layers around the first pixel and the second pixel to respectively form an overhead first light tunnel toward the first pixel and a stepped second light tunnel toward the second pixel to cause the first pixel and the second pixel to receive the emergent light from the skin region at different first and second light receiving angles respectively, and the different first and second light receiving angles define the at least one signal source parameter;

calculating, by the physiological detection module, a first confident level according to the image signal;

outputting, by the physiological detection module, an intensity variation signal according to a plurality of image signals;

calculating, by the application module, a second confident level according to the intensity variation signal; and updating the at least one signal source parameter according to the first confident level and the second confident level.

17. The operating method as claimed in claim 16, wherein the first confident level comprises at least one of an average brightness value and uniformity, and the second confident level comprises at least one of a PPG signal amplitude and a signal to noise ratio.

18. The operating method as claimed in claim 16, wherein
the at least one signal source parameter further comprises at least one of an exposure time, a gain value, a window of interest, and a focus length, and
the window of interest is a pixel area of the physiological detection module having a higher confident level than other pixels or having brightness within a predetermined range.

19. The operating method as claimed in claim 16, further comprising:
calculating, by the application module, physiological characteristics according to the intensity variation signal.

20. The operating method as claimed in claim 16, further comprising:
adjusting a light emitting intensity of a light source of the physiological detection module according to the at least one signal source parameter.

* * * * *